US008481787B2

(12) United States Patent
Nishimura et al.

(10) Patent No.: US 8,481,787 B2
(45) Date of Patent: Jul. 9, 2013

(54) METHOD FOR PRODUCING TERTIARY AMINE

(75) Inventors: Toru Nishimura, Wakayama (JP); Wataru Nomura, Wakayama (JP); Yushin Takahashi, Emmerich (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/514,254

(22) PCT Filed: Dec. 20, 2010

(86) PCT No.: PCT/JP2010/072845
§ 371 (c)(1),
(2), (4) Date: Jul. 12, 2012

(87) PCT Pub. No.: WO2011/078100
PCT Pub. Date: Jun. 30, 2011

(65) Prior Publication Data
US 2012/0277470 A1    Nov. 1, 2012

(30) Foreign Application Priority Data

Dec. 22, 2009  (JP) ................................. 2009-290030
Dec. 8, 2010   (JP) ................................. 2010-273331

(51) Int. Cl.
C07C 209/14   (2006.01)
C07C 209/16   (2006.01)
C07C 209/18   (2006.01)

(52) U.S. Cl.
USPC .......................................... 564/480; 564/479

(58) Field of Classification Search
USPC .................................... 564/479, 480
See application file for complete search history.

(56) References Cited

U.S. PATENT DOCUMENTS

| 3,804,901 A * | 4/1974 | Noeske et al. ................. 549/491 |
| 4,625,063 A * | 11/1986 | Yokota et al. ................. 564/480 |
| 4,806,287 A | 2/1989 | Sulc et al. |
| 5,266,730 A | 11/1993 | Abe et al. |
| 7,615,666 B2 * | 11/2009 | Nishimura et al. ........... 564/479 |
| 2007/0232833 A1 | 10/2007 | Haese et al. |
| 2008/0004472 A1 | 1/2008 | Nishimura et al. |
| 2009/0030236 A1 | 1/2009 | Nishimura et al. |
| 2009/0264652 A1 | 10/2009 | Kubanek et al. |
| 2010/0217044 A1 | 8/2010 | Nomura et al. |

FOREIGN PATENT DOCUMENTS

| EP | 0281417 A2 | 9/1988 |
| JP | 61-15865 A | 1/1986 |
| JP | 64-13060 A | 1/1989 |
| JP | 2-234 A | 1/1990 |
| JP | 6-239809 A | 8/1994 |
| JP | 2006-312624 A | 11/2006 |
| JP | 2007-537177 A | 12/2007 |
| JP | 2009-73754 A | 4/2009 |
| JP | 2009-543830 A | 12/2009 |
| WO | WO 2005/035122 A1 | 4/2005 |
| WO | WO 2005/110969 A1 | 11/2005 |
| WO | WO 2006-109848 A1 | 10/2006 |
| WO | WO 2008/006748 A1 | 1/2008 |

OTHER PUBLICATIONS

Official Action for forresponding German Patent Application No. 11 2010 004 959.9, dated Oct. 15, 2012.
International Search Report issued in PCT/JP2010/072845, mailed on Feb. 8, 2011.
Written Opinion of the International Searching Authority issued in PCT/JP2010/072845, mailed on Feb. 8, 2011.
Decision for patent issued in JP Patent Application No. 2010-273331, mailed on Feb. 21, 2012.
International Preliminary Report on Patentability, and Translation of Written Opinion of the International Searching Authority, dated Jul. 4, 2012, for International Application No. PCT/JP2010/072845 (Forms PCT/IB/373 and PCT/ISA/237).

* cited by examiner

*Primary Examiner* — Brian J Davis
(74) *Attorney, Agent, or Firm* — Birch, Stewart, Kolasch & Birch, LLP

(57) ABSTRACT

The present invention provides a method for producing a tertiary amine by using a secondary amine and an alcohol as starting materials to obtain a corresponding tertiary amine. The method of the present invention includes reacting a secondary amine with an alcohol in the presence of a catalyst, wherein the catalyst is previously used in the reaction of a primary amine with an alcohol to obtain a tertiary amine.

18 Claims, 1 Drawing Sheet

METHOD FOR PRODUCING TERTIARY AMINE

FIELD OF THE INVENTION

The present invention relates to a method for producing a tertiary amine.

BACKGROUND OF THE INVENTION

Aliphatic amines produced from beef tallow, coconut oil, palm oil, and the like are important intermediates for household and industrial products. In particular, aliphatic tertiary amines are derived into a quaternary ammonium salt or the like to be used in various applications such as fabric softener, antistatic agent, and rinse base.

There are known methods for producing a tertiary amine, including a reaction of a primary or secondary amine with an alcohol in the presence of a catalyst to obtain a corresponding tertiary amine.

Such a method, however, has a problem of a decreased yield of a product due to generation of a considerable amount of side-products, in particular when a secondary amine is a starting material to produce a corresponding tertiary amine, or a mono-substituted tertiary amine by substituting a hydrogen atom attached to the nitrogen atom of the secondary amine with an alkyl group and/or an alkenyl group derived from an alcohol.

Examples of the side-product include other tertiary amines derived from a primary amine and ammonia generated by side-reactions of the starting secondary amine through reactions with the alcohol, or di-substituted tertiary amines having two alkyl and/or alkenyl groups attached to the nitrogen atom derived from the starting alcohol and tri-substituted tertiary amines having three alkyl and/or alkenyl groups attached to the nitrogen atom. In order to increase a yield of an intended tertiary amine, reduction of generation of these side-products is important.

For example, JP-A No. 61-015865 discloses a method for producing a tertiary amine using a platinum group element catalyst having a copper-nickel-Group 8 element system (referring to the Group VIII by old IUPAC, corresponding to Groups 8 to 10 by current IUPAC).

WO-A 2005/035122 discloses a method for producing a tertiary amine using an immobilized catalyst in a film form having a thickness of not more than 500 μm as a process in which complicated operations such as stirring of a slurry and separation of the catalyst from the slurry after the reaction by filtration or the like can be omitted, the slurry being generated with a powder catalyst in producing a tertiary amine.

SUMMARY OF THE INVENTION

The present invention relates to a method for producing a tertiary amine, including reacting a secondary amine with an alcohol in the presence of a catalyst, wherein the catalyst is previously used in a reaction of a primary amine with an alcohol to obtain a tertiary amine.

DETAILED DESCRIPTION OF THE INVENTION

The method of JP-A No. 61-015865 provides insufficient yield of an intended mono-substituted tertiary amine from a secondary amine due to insufficient control of generation of side-products.

The method of WO-A 2005/035122 may also produce side-products other than an intended mono-substituted tertiary amine when a secondary amine is used as a starting material to obtain a tertiary amine. In addition, the method should be further studied for developing a more industrially advantageous method using a secondary amine as a starting material.

The present invention provides the method using a secondary amine and an alcohol as starting materials to produce a corresponding tertiary amine at high efficiency.

According to the present invention, an intended tertiary amine can be produced at high efficiency.

Figure 1:
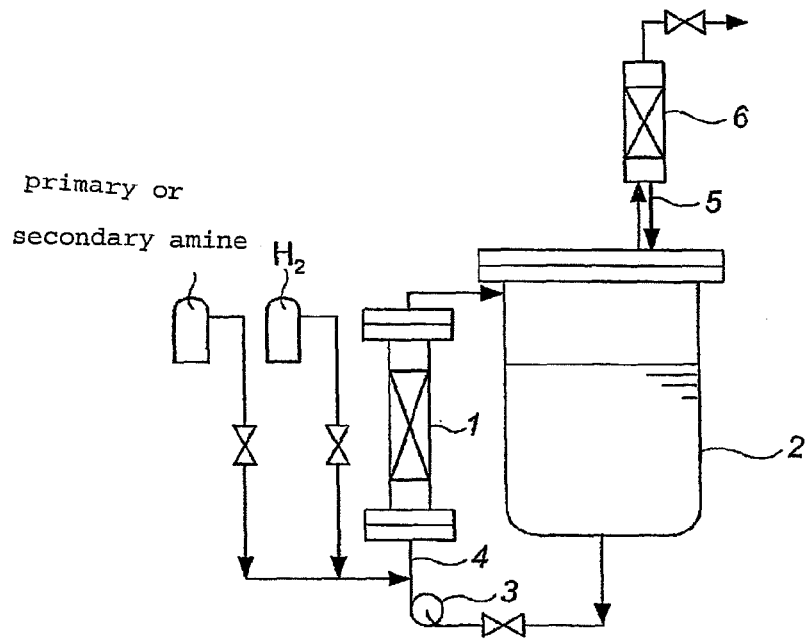
FIG. 1 shows a schematic diagram of an example of the fixed-bed circulation reactor used in the present invention.

In figures, the reference numerals are assigned as follows:

| | |
|---|---|
| 1: | Tubular reactor loaded with a film catalyst |
| 2: | Buffer tank |
| 3: | External circulation pump |
| 4: | Conduit for external circulation |
| 5: | Conduit for packed column |
| 6: | Packed column |
| 21: | Stirred tank |
| 22: | Agitator |
| 23: | Impeller |
| 24: | Gas sparger |
| 25: | Conduit for packed column |
| 26: | Packed column |

In the present invention, the starting alcohol used in either reaction is preferably a linear or branched, saturated or unsaturated aliphatic alcohol having 8 to 36 carbon atoms. Examples of the alcohol include octyl, decyl, lauryl, myristyl, stearyl, behenyl, and oleyl alcohols, mixed alcohols thereof, Ziegler alcohols produced by the Ziegler method, oxo alcohols produced by the oxo method, and Guerbet alcohols.

The starting primary amine used in the present invention is preferably an aliphatic primary amine having one alkyl group having 1 to 18 carbon atoms, more preferably 1 to 4 carbon atoms. Examples of the primary amine include monomethylamine, monoethylamine, and monododecylamine. Among these amines, the primary amine is preferably selected from monomethylamine and monoethylamine.

The starting secondary amine used in the present invention is preferably an aliphatic secondary amine having two alkyl groups each having 1 to 18 carbon atoms, more preferably 1 to 4 carbon atoms. Examples of the secondary amine include dimethylamine, diethylamine, and didodecylamine. Among these amines, the secondary amine is preferably selected from dimethylamine and diethylamine.

The corresponding tertiary amine is produced from these starting primary or secondary amine and alcohol by substitution of a hydrogen atom on the nitrogen atom of the primary or secondary amine with an alkyl and/or alkenyl group derived from the alcohol. For example, a corresponding tertiary amine produced from dimethylamine and lauryl alcohol is N-dodecyl-N,N-dimethylamine. The corresponding tertiary amine is distinguished from tertiary amines, which are N,N-didodecyl-N-methylamine and N,N,N-tridodecylamine produced by side reactions of methylamine and ammonia with lauryl alcohol respectively. Methylamine and ammonia are side-products from dimethylamine.

Any known catalyst can be used in the present invention if it enables a primary or secondary amine and an alcohol to react and obtain a tertiary amine. In general, Cu group metals are preferably used. Examples of the catalyst include those of Cu single component, two components of Cu and a transition metal element such as Cr, Co, Ni, Fe, or Mn, and three or more components. These catalysts may be supported on silica, alumina, titania, zeolite, or the like.

For a high activity, a high selectivity, and a high durability of the catalyst used in the present invention, the catalyst preferably contains Cu and/or Ni, and more particularly has a composition containing Cu, Ni, and at least one element selected from Pt, Pd, Ru, and Rh in the platinum group elements of Groups 8 to 10, wherein a molar ratio of metal atoms Cu:Ni is 1:9 to 9:1, and a molar ratio of the platinum group element of Groups 8 to 10 to the total of Cu and Ni is 0.0001 to 0.1.

The catalyst used can have various forms, including granule, powder, or an immobilized form, such as pellets, noodles, honeycomb or monolith. The catalyst in a granule or powder form can be used by suspending in a fluid containing starting materials. The catalyst in an immobilized form can be used by loading therewith the reactor which is supplied with a fluid containing starting materials.

Among various forms of an immobilized catalyst, a film form can be preferably used. Examples of the film catalyst include that described in Patent Reference 2. The film catalyst refers to a catalyst in the form of a thin film having a thickness of not more than 500 μm, differing from a conventional packed-bed catalyst irregular in shape having several millimeters. Use of the film catalyst enables to simplify a process due to unnecessity of an operation for separating the catalyst, resulting in efficient production of an intended tertiary amine. For a method of producing the film catalyst, it is preferable to form a film of coating containing a catalytically active powder and a binder such as a synthetic resin for fixing it on a support.

A thickness of the film catalyst is preferably not more than 100 μm, and more preferably not more than 50 μm. At a thickness within this range, the catalyst can prevent overreaction of an intermediate in the catalyst and also has an increased reactivity per mass of the catalyst. Forgetting strength of a catalyst layer and durability in strength, the catalyst preferably has a thickness of not less than 0.01 μm, and more preferably not less than 1 μm.

The reactor can have various forms including known forms. Examples of the reactor include a tubular flow reactor and a tank reactor. In the tubular reactor, the reaction can proceed in a continuous way or a batchwise way, by a single time circulation or a circulating feeding, by a method of supplying reactants to the immobilized catalyst in the tube and continuously collecting a product or a method of feeding a suspension fluid of a granule or powder catalyst containing reactants to the tube and continuously collecting a product. In the tank reactor, the reaction can proceed in a continuous way or a batchwise way by mixing a fluid containing reactants with stirring or the like.

Before reacting the primary or secondary amine with the alcohol, the catalyst can be preferably reduced and activated. The reduction of the catalyst is preferably performed, in the reactor in which the catalyst is loaded, by supplying a hydrogen gas to the reactor, and more preferably in the presence of the starting alcohol. The reduction is specifically conducted by feeding the starting alcohol containing the granular or powder catalyst suspended therein to the reactor and supplying a hydrogen gas to the reactor, by supplying a hydrogen gas and the starting alcohol to the reactor loaded with the film catalyst, or by feeding the starting alcohol in the reactor loaded with the film catalyst and supplying a hydrogen gas.

Conditions for the reaction with the alcohol in the presence of the catalyst depend on types of reactant, product, and catalyst. The reactant may be present in a gas or liquid phase. In the gas-liquid two-phase reaction system, if the alcohol and the primary or secondary amine are separately present in different phases, respectively, mass transfer between the phases is desirably promoted by bubbling the gas in the liquid or the like. Hydrogen is desirably supplied into the reaction system for the reaction to proceed favorably with the production of the tertiary amine, for example, by maintaining the activity of the catalyst etc. In addition, an inactive gas to amination such as nitrogen and a noble gas may also be supplied. A supply amount of the primary or secondary amine is desirably adjusted according to progress of the reaction to reduce an excess amount of the primary or secondary amine for improvement in quality and yield of an amine product. The supply amount is specifically adjusted to such an amount as that the primary or secondary amine accounts for not more than 50% by volume (to exhaust gas), and more preferably not more than 30% by volume, in a gas exhausted from the reaction system excluding generated water. It is preferable that a pressure in the system does not increase remarkably beyond the ambient pressure. A reaction temperature, which may depend on a kind of catalyst, is preferably within the range of 150 to 300° C. Water generated as a side-product during the course of the reaction is removed off from the reaction system, thereby promoting progress of the reaction and maintaining an activity of the catalyst. Progress of the reaction can be monitored by, for example, gas chromatography.

In the present invention, before a reaction of a secondary amine with an alcohol in the presence of a catalyst to obtain a tertiary amine, a reaction of a primary amine with an alcohol in the presence of the catalyst to obtain a tertiary amine is performed so that an intended mono-substituted tertiary amine may be obtained at high yield.

In the reaction of a primary amine with an alcohol before the reaction of a secondary amine with an alcohol, the starting alcohol may be same to or different from that used in the subsequent reaction of a secondary amine. A produced di-substituted tertiary amine desirably has a significant potential in industry. The alcohol thus can be appropriately selected so as to provide an alkyl and/or alkenyl group fitting the purpose. From this viewpoint, preferred conditions for the reaction of a primary amine with an alcohol are as follows: a molar ratio of them used, primary amine/alcohol, is 0.5 to 3, and more preferably 0.5 to 1.5; a reaction temperature is 100 to 250° C., and more preferably 180 to 230° C.; a reaction pressure is the ambient pressure to 10 atmospheres, and more preferably the ambient pressure to 5 atmospheres; and, a reaction time is 1 to 10 hours, more preferably 2 to 8 hours, and even more preferably 2 to 7 hours. In the reaction, the catalyst is preferably used in the form of film, in an effective amount of 0.1 to 10% by mass to an amount of the starting alcohol, containing Cu, Ni, and at least one element selected from Pt, Pd, Ru, and Rh of the platinum group elements of Groups 8 to 10, at a molar ratio of Cu:Ni of 1:9 to 9:1, at a molar ratio of the platinum group element to the total of Cu and Ni of 0.0001 to 0.1.

Preferred conditions for the reaction of a secondary amine with an alcohol are as follows: a molar ratio of them used, secondary amine/alcohol, is 1 to 5, and more preferably 1 to 3; a reaction temperature is 100 to 250° C., and more preferably 180 to 230° C.; a reaction pressure is the ambient pressure to 10 atmospheres, and more preferably ambient pressure to 5 atmospheres; and, a reaction time is 1 to 10 hours, and more preferably 2 to 6 hours. In the reaction, the catalyst is preferably used in the form of film, in an effective amount of 0.1 to 10% by mass to an amount of the starting alcohol, containing Cu, Ni, and at least one element selected from Pt, Pd, Ru, and Rh of the platinum group elements of Groups 8 to 10, at a molar ratio of Cu:Ni of 1:9 to 9:1, at a molar ratio of the platinum group element of Groups 8 to 10 to the total of Cu and Ni of 0.0001 to 0.1. In the present invention, (A) a tertiary amine is produced by reacting a primary amine with an alcohol in the presence of a catalyst and (B) an intended tertiary amine is produced by reacting a secondary amine with a separately prepared alcohol in the presence of the catalyst used in production of (A). The tertiary amine (A) has two hydrocarbon groups derived from the alcohol, while the tertiary amine (B) has one hydrocarbon group derived from the alcohol.

A mechanism is not yet known that use of the catalyst previously used in the reaction of a primary amine with an alcohol increases a yield of an intended tertiary amine from the reaction of a secondary amine with an alcohol. It is considered that some chemical change may happen in the catalyst through the reaction of the primary amine with the alcohol. For example, the primary amine is expected to tightly adsorb on the catalyst at an active site where a primary amine is produced in a side reaction of the secondary amine and the secondary amine will be avoided from the side reaction. It is possible, based on this standpoint, to achieve the same effect as that obtained by the reaction of the primary amine with the alcohol by only exposing the catalyst to the primary amine. Another expected mechanism is as follows. A di-substituted tertiary amine produced by the reaction of the primary amine with the alcohol tightly adsorbs on the surface of the catalyst. Steric hindrance by two alkyl and/or alkenyl groups of the di-substituted tertiary amine prevents the di-substituted tertiary amine from newly being produced on the surface of the catalyst. It is possible, based on this standpoint, to achieve the same effect to that obtained by the reaction of the primary amine with the alcohol only by exposing the catalyst to the di-substituted tertiary amine.

The subsequent reaction of a secondary amine with an alcohol after the reaction of a primary amine with an alcohol to produce a tertiary amine can be performed with the same catalyst in the same equipment, or with the same catalyst recovered from the previous reaction in another equipment. The catalyst may be recovered and used fully or partially. Alternatively, catalysts separately used in several batches of the reaction of the primary amine with the alcohol are collected to obtain a masterbatch. All or part of the masterbatch may be used in the reaction of a secondary amine with an alcohol. For each of reactions of the primary amine and the secondary amine with respective alcohols, a method and an amount of recovery of the catalyst can be appropriately selected in consideration of a batch size of the reaction or a throughput in a sequence of reactions, an amount of catalyst required, a production volume and a shipment time of a tertiary amine, and the like.

In the case of using an immobilized catalyst such as a film catalyst, the reaction of a primary amine with an alcohol and then the reaction of a secondary amine with an alcohol can be appropriately conducted consecutively in the same equipment to obtain a tertiary amine.

The di-substituted tertiary amine produced in the reaction of the primary amine with the alcohol is different from the mono-substituted tertiary amine to be produced in the subsequent reaction of the secondary amine with the alcohol. A product mixture containing the di-substituted tertiary amine is collected from the reaction system including the reactor and an ancillary apparatus such as that for filtrating the catalyst, but the residue in such equipments may decrease the purity of the tertiary amine to be produced in the subsequent reaction. Particularly when the di-substituted tertiary amine is difficult to be separated and removed from a mono-substituted tertiary amine produced by the reaction of a secondary amine with an alcohol in a step of purifying the mono-substituted tertiary amine, the reacted mixture is desirably collected from the reaction system in the recovery rate as high as possible before the reaction of the secondary amine with the alcohol. In order to sufficiently reduce effects of the residue in the equipment, the reaction of the secondary amine with the alcohol is also preferably conducted continuously or sequentially for a sufficient period of time to produce a considerable amount of the mono-substituted tertiary amine.

In the case of using different alcohols for the reaction of the secondary amine and the preceding reaction of the primary amine in the same equipment, a residue in a supply system of the starting material may decrease the purity of a starting alcohol for the next reaction. Decreased purity of the starting alcohol results in decreased purity of a mono-substituted tertiary amine through the reaction of a secondary amine with the alcohol. To remove effects of the residue in the supply system, the starting alcohol used in the reaction of the secondary amine is preferably same to that used in the preceding reaction of the primary amine. In order to sufficiently reduce effects of the residue in the supply system, the reaction of the secondary amine with the alcohol is also preferably conducted continuously or sequentially for a sufficient period of time to produce a considerable amount of the mono-substituted tertiary amine.

The method of the present invention can efficiently produce a tertiary amine from corresponding secondary amine and alcohol. In many cases, a tertiary amine produced by the reaction of a primary amine with an alcohol is industrially useful, and thus the method of the present invention is also useful as a method for producing different two tertiary amines.

EXAMPLES

The following examples further describe and demonstrate embodiments of the present invention. The examples are given solely for the purpose of illustration and are not to be construed as limitations of the present invention.

Preparation Example 1

Preparation of Film Catalyst A

A film catalyst A was prepared by fixing a powder catalyst with a phenol resin as a binder as described below.

A 1 L flask was charged with a synthetic zeolite and then an aqueous solution of copper nitrate, nickel nitrate, and ruthenium chloride at a molar ratio of metal elements of Cu:Ni:Ru=4:1:0.01. A mixture was heated with stirring. 10% by mass aqueous solution of sodium carbonate was gradually added dropwise to the mixture at 90° C. with keeping pH from 9 to 10. The mixture was stirred for 1 hour. Then, a precipitate was filtered, washed with water, dried for 10 hours at 80° C., and calcined for 3 hours at 600° C. to obtain a powder catalyst. In the powder catalyst, a percentage of metal oxides was 50% by mass, and a percentage of the synthetic zeolite was 50% by mass.

To 100 parts by mass of the powder catalyst were added a phenol resin (Sumitomo Bakelite Co., Ltd., PR-9480, non-volatile content: 58%) as a binder in such an amount to meet 25 parts by mass of the non-volatile content of the phenol resin. Then MIBK (methylisobutylketone) was added as a solvent in such amount as a proportion of solid matters (the powder catalyst and the nonvolatile content of the phenol resin) was 60%. The mixture was pre-mixed for 30 minutes with a disperser, and mixed and dispersed for 40 minutes at 600 rpm with a basket mill (Asada Iron Works Co., Ltd., SS-10, filled with 4.8 L (7.2 kg) of 1.6 mm glass beads) to obtain a coating. A copper foil (thickness: 40 µm) as a substrate was coated with the coating at a coating speed of 20 m/min with a gravure coater so as to make the coated film having a thickness of 13 µm. It was passed through a drying furnace (temperature: 130° C., residence time: 15 seconds) and rolled up. The opposite side of the foil was subjected in the same way to form coated films on both sides.

A part of the resultant foil corresponding to 0.266 m² of dry coated film on one side was cut into strips having a width of 130 mm. A half of the strips were folded to form corrugated sheets.

Both folded and plane strips were cured for 90 minutes at 150° C. in a hot-air circulating dryer, thereby fixing a film catalyst on the copper foil on both sides. The resultant film catalysts had a thickness of 13 µm per one side, excluding the foil and the total mass of 20.9 g per square meter per one side.

In the following Example 1 and Comparative Example 1, used were a fixed-bed circulation reactor shown in FIG. 1 and dimethyl amine and lauryl alcohol as starting materials to prepare N-dodecyl-N,N-dimethylamine. In Example 1, before the reaction, the same reactor was used to prepare N,N-didecyl-N-methylamine from monomethylamine and decyl alcohol. In the following description, unless otherwise sited, "%" refers to "% by mass". In table 1, conditions for reacting the secondary amine with the alcohol and others in Example 1 and Comparative Example 1 are listed.

In FIG. 1, a tubular reactor 1 loaded with a film catalyst is a fixed-bed reactor in a vertical cylindrical shape. The film catalyst is loaded in the reactor. The reactor can be thermally controlled with external heat source. A buffer tank 2 is for storing a liquid reactant and/or a liquid product mixture. An external circulation pump 3 circulates the liquid between the reactor 1 and the tank 2. A conduit for external circulation 4 is for continuously supplying the reactant and/or the mixture of products, a gaseous primary or secondary amine, and a hydrogen gas from the bottom of the reactor 1. From the top of the reactor, unreacted materials and/or a mixture of products, and a hydrogen gas are continuously collected to be introduced in the buffer tank 2. A conduit for packed column 5 is for continuously exhausting an unreacted gaseous primary or secondary amine and water. As well as these components, an exhausted gas from the conduit 5 may further contain an alcohol and/or a generated tertiary amine in a vapor or a mist form. A packed column 6 is for liquefying and returning them to the buffer tank 2. The other gaseous component is exhausted from the system. The inside of the reaction system is kept to almost ambient pressure.

Example 1

The film catalyst A prepared in Preparation Example 1 was loaded in the reactor 1 having an inner diameter of 28.4 mm. A volume of the part of the reactor in which the film catalyst was loaded was 0.25 L. The film catalyst formed plural flow passages each having a cross-section area of about 0.1 cm² and communicating through the axial direction of the reactor 1.

<Reduction of Catalyst>

600 g of lauryl alcohol (Kao Corporation, Kalcol 2098) was fed in the buffer tank 2. With supplying hydrogen gas at a flow rate of 16.5 L/Hr in terms of volume under standard conditions, the alcohol was circulated at 5.92 L/Hr between the buffer tank 2 and the reactor 1. At this state, the inside temperature of the reactor 1 was elevated to 130° C. and held at the temperature for 6 hours to reduce the catalyst. Then, the whole system was cooled, and all the alcohol was removed.

<Preparation of N,N-didecyl-N-methylamine from Monomethylamine and Decyl Alcohol>

660 g of decyl alcohol (Kao Corporation, Kalcol 1098) was fed in the buffer tank 2. With supplying a hydrogen gas at a flow rate of 9.9 L/Hr in terms of volume under standard conditions, the alcohol was circulated at 5.92 L/Hr between the buffer tank 2 and the reactor 1. The inside temperature of the reactor 1 was elevated to 165° C., and monomethylamine was supplied to the reactor 1. The inside temperature of the reactor 1 was further elevated to 192° C. to start the reaction. Monomethylamine was supplied in the feeding amount, adjusted according to progress of the reaction, of 17 g/Hr on the average in view of the reaction time. After 7 hours from the start of the reaction, the supplying of monomethylamine was stopped, and the whole system was cooled. All the liquid in the buffer tank 2 and the reactor 1 was collected. The collected liquid was analyzed by gas chromatography. The result of quantification by the area percentage method showed that: 2.6% of unreacted decyl alcohol, 89.6% of N,N-didecyl-N-methylamine, 0.7% of N-decyl-N,N-dimethylamine, and 0.8% of N,N,N-tridecylamine, which were generated.

<Preparation of N-dodecyl-N,N-dimethylamine from Dimethylamine and Lauryl Alcohol>

The same reactor 1 was used with the used film catalyst still loaded. 600 g of lauryl alcohol (Kao Corporation, Kalcol 2098) was charged in the buffer tank 2. With supplying a hydrogen gas at a flow rate of 16.5 L/Hr in terms of volume under standard conditions, the alcohol was circulated at 5.92 L/Hr between the buffer tank 2 and the reactor 1. The inside temperature of the reactor 1 was elevated to 185° C., and dimethylamine was supplied to the reactor 1. The inside temperature of the reactor 1 was further elevated to 220° C. to start the reaction. Dimethylamine was supplied in a feeding amount, adjusted according to progress of the reaction, of 51 g/Hr on the average in view of the reaction time. After 2.6 hours from the start of the reaction, the feeding of dimethylamine was stopped, and the whole system was cooled. All the liquid in the buffer tank 2 and the reactor 1 was collected. The collected liquid was analyzed by gas chromatography to quantify by the area percentage method. Results showed that: 0.8% of unreacted lauryl alcohol, 91.2% of N-dodecyl-N,N-dimethylamine, and 4.7% of N,N-didodecyl-N-methylamine, which were generated. N,N,N-tridodecylamine was not detected.

Comparative Example 1

In the same way as in Example 1, the film catalyst A prepared in Preparation Example 1 was loaded in the inside of the reactor 1 and reduced by the same operation as in the Example 1.

<Preparation of N-dodecyl-N,N-dimethylamine from Dimethylamine and Lauryl Alcohol>

600 g of lauryl alcohol (Kao Corporation, Kalcol 2098) was fed in the buffer tank 2. With supplying a hydrogen gas at a flow rate of 16.5 L/Hr in terms of volume under standard conditions, the alcohol was circulated at 5.92 L/Hr between the buffer tank 2 and the reactor 1. The inside temperature of the reactor 1 was increased to 185° C., and dimethylamine was supplied to the reactor 1. The inside temperature of the reactor 1 was further elevated to 220° C. to start the reaction. Dimethylamine was supplied in a feeding amount, adjusted according to progress of the reaction, of 42 g/Hr on the average in view of the reaction time. After 3.3 hours from the start of the reaction, the feeding of dimethylamine was stopped, and the whole system was cooled. All the liquid in the buffer tank 2 and the reactor 1 was collected. The collected liquid was analyzed by gas chromatography to quantify by the area percentage method. Results showed that: 0.5% of unreacted lauryl alcohol, 78.9% of N-dodecyl-N,N-dimethylamine, and 17.2% of N,N-didodecyl-N-methylamine, which were generated. N,N,N-tridodecylamine was not detected.

TABLE 1

| | | Reaction conditions | | | Content in reactant (% by mass) | | |
|---|---|---|---|---|---|---|---|
| | Catalyst history | Amount of catalyst (% by mass to starting material) | Reaction time (hours) | Reaction temperature (° C.) | Unreacted alcohol | Intended product DM type | side product M2 type | M type |
| Example 1 | Previously used in the preceding reaction | 1.5 | 2.6 | 220 | 0.8 | 91.2 | 4.7 | 0.1 |
| Comparative example 1 | Not used in the preceding reaction | 1.5 | 3.3 | 220 | 0.5 | 78.9 | 17.2 | 0.6 |

In Table 1, the "pre-reaction" refers to the reaction of a primary amine with an alcohol; the "DM type" refers to a dimethyl-having tertiary amine, which is "N-dodecyl-N,N-dimethylamine" in above examples; the "M2 type" refers to di (long-chain alkyl)- having tertiary amine, which is "N,N-didodecyl-N-methylamine" in above examples; the "M type" refers to a monomethyl-mono (long-chain alkyl)- secondary amine, which is "N-dodecyl-N-methylamine" in above Examples; and "% by mass to starting material" of a catalyst amount refers to "% by mass to starting alcohol" in Table 1.

Preparation Example 2

Preparation of Powder Catalyst B

A powder catalyst B was prepared as described below.
A 1 L flask was charged with a synthetic zeolite and then an aqueous solution of copper nitrate, nickel nitrate, and ruthenium chloride at a molar ratio of metal elements of Cu:Ni:Ru=4:1:0.01. A mixture was heated with stirring. 10% by mass aqueous solution of sodium carbonate was gradually added dropwise to the mixture at 90° C. with keeping pH from 9 to 10. The mixture was stirred for 1 hour. Then, a precipitate was filtered, washed with water, dried for 10 hours at 80° C., and calcined for 3 hours at 600° C. to obtain a powder catalyst. In the powder catalyst, a percentage of metal oxides was 50% by mass, and a percentage of the synthetic zeolite was 50% by mass.

In the following Example 2 and Comparative Example 2, used were a stirred tank reactor shown in FIG. 2 and dimethyl amine and lauryl alcohol as starting materials to prepare N-dodecyl-N,N-dimethylamine. In Example 2, before the reaction, the same reactor was used to prepare N,N-didecyl-N-methylamine from monomethylamine and decyl alcohol. In the following description, unless otherwise sited, "%" refers to "% by mass". In table 2, conditions for reacting the secondary amine with the alcohol and the like in Example 2 and Comparative Example 2 were listed.

Figure 2:
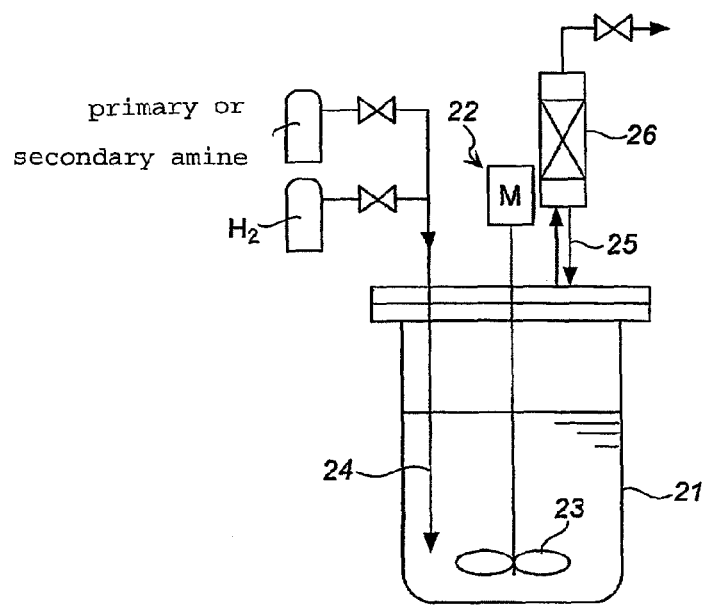
FIG. 2 shows a schematic diagram of an example of the stirred tank reactor used in the present invention.

In FIG. 2, a stirred tank 21 contains a slurry of a mixture of liquid reactants in which the powder catalyst was dispersed and/or products. The content of the tank 21 is mixed with an impeller 23 connected to an agitator 22 and the temperature of the stirred tank 21 can be thermally controlled with external heat source. A gas sparger tube 24 is for continuously supplying a gaseous primary or secondary amine and hydrogen gas into the stirred tank 21. A conduit for packed column 25 is for continuously exhausting an unreacted gaseous primary or secondary amine and water. As well as these components, a exhausted gas from the conduit 25 may further contain an alcohol and/or a generated tertiary amine in a vapor or a mist form. A packed column 26 is for liquefying and returning them to the stirred tank 21. The other gaseous component is exhausted from the system. The inside of the system is kept almost at the ambient pressure.

Example 2

Reduction of Catalyst 1200 g of decyl alcohol (Kao Corporation, Kalcol 1098) and then 6.0 g of the powder catalyst B prepared in Preparation Example 2 were fed in the stirred tank 21. With supplying a hydrogen gas at a flow rate of 18 L/Hr in terms of volume under standard conditions, the content was stirred and mixed at 1000 rpm with the impeller 23. At this state, the inside temperature of the stirred tank 21 was elevated to 180° C. and held at the temperature for 1 hour to reduce the catalyst.

<Preparation of N,N-didecyl-N-methylamine from Monomethylamine and Decyl Alcohol>

Following the reduction of the powder catalyst B, a hydrogen gas was supplied at a flow rate of 18 L/Hr in terms of volume under standard conditions to the stirred tank 21, monomethylamine was supplied and then the inside temperature of the stirred tank 21 was elevated to 192° C. to initiate the reaction. Monomethylamine was supplied in the amount, adjusted according to progress of the reaction, of 26 g/Hr on the average in view of the reaction time. After 3.9 hours from the start of the reaction, the feeding of monomethylamine was stopped, and the whole system was cooled. All the liquid and the catalyst in the stirred tank 21 were collected. The catalyst was separated by filtration. The filtrate was analyzed by gas chromatography to quantify by the area percentage method. Results showed that: 3.2% of unreacted decyl alcohol, 93.1% of N,N-didecyl-N-methylamine, 0.3% of N-decyl-N,N-dimethylamine, and 0.5% of N,N,N-tridecylamine, which were generated.

<Preparation of N-dodecyl-N,N-dimethylamine from Dimethylamine and Lauryl Alcohol>

Two-thirds (corresponding to 4.0 g) of the powder catalyst that have been used in the preparation of N,N-didecyl-N-methylamine and separated by filtration and 1200 g of lauryl alcohol (Kao Corporation, Kalcol 2098) were fed in the stirred tank 21. With supplying a hydrogen gas at a flow rate of 13 L/Hr in terms of volume under standard conditions, the content of the stirred tank 21 was stirred and mixed at 1000 rpm with the impeller 23. The inside temperature of the stirred tank 21 was elevated to 190° C., and dimethylamine was supplied to the reactor to start the reaction. While increasing the temperature in the stirred tank 21 to 220° C., a flow rate of hydrogen gas was increased to 27 L/Hr in terms of volume under standard conditions. Dimethylamine was supplied in the amount, adjusted according to progress of the reaction of 93 g/Hr on the average in view of the reaction time. After 2.3 hours from the start of the reaction, a sample of the liquid in the stirred tank 21 was taken and analyzed by gas chromatography to quantify by the area percentage method. Results showed that: 1.7% of unreacted lauryl alcohol, 93.3% of N-dodecyl-N,N-dimethylamine, and 3.7% of N,N-didodecyl-N-methylamine, which were generated. N-dodecyl-N-methylamine and N,N,N-tridecylamine were not detected. The reaction further continued. After 2.6 hours from the start of the reaction, the feeding of dimethylamine was stopped, and the whole system was cooled. All the liquid in the stirred tank 21 was collected. The catalyst was separated by filtration. The filtrate was analyzed by gas chromatography to quantify by the area percentage method. Results showed that: 1.0% of unreacted lauryl alcohol, 93.8% of N-dodecyl-N,N-dimethylamine, and 3.8% of N,N-didodecyl-N-methylamine, which were generated. N-dodecyl-N-methylamine and N,N,N-tridodecylamine were not detected.

Comparative Example 2

Reduction of Catalyst

In the same way as in Example 2, 4.0 g of powder catalyst B prepared in Preparation Example 2 was fed in the stirred tank 21 and reduced by the same operation as in Example 2.

<Preparation of N-dodecyl-N,N-dimethylamine from Dimethylamine and Lauryl Alcohol>

1200 g of lauryl alcohol (Kao Corporation, Kalcol 20) and all of the powder catalyst B reduced were fed in the stirred tank 21. With supplying a hydrogen gas at a flow rate of 13 L/Hr in terms of volume under standard conditions, the content of the stirred tank 21 was stirred and mixed at 1000 rpm with the impeller 23. The inside temperature of the stirred tank 21 was elevated to 190° C., and dimethylamine was supplied to the reactor to start the reaction. With further elevating the temperature in the stirred tank 21 to 220° C., a flow rate of a hydrogen gas was increased to 27 L/Hr in terms of volume under standard conditions. Dimethylamine was supplied in the amount, adjusted according to progress of the reaction, of 98 g/Hr on the average in view of the reaction time. After 2.3 hours from the start of the reaction, the feeding of dimethylamine was stopped, and the whole system was cooled. All the liquid in the stirred tank 21 was collected. The catalyst was separated by filtration. The filtrate was analyzed by gas chromatography to quantify by the area percentage method. Results showed that:

1.0% of unreacted lauryl alcohol, 93.1% of

N-dodecyl-N,N-dimethylamine, and 5.5% of

N,N-didodecyl-N-methylamine, which were generated.

N-dodecyl-N-methylamine and N,N,N-tridodecylamine were not detected.

TABLE 2

| | | Reaction conditions | | | Content in reactant(% by mass) | | |
|---|---|---|---|---|---|---|---|
| | Catalyst history | Amount of catalyst (% by mass to starting material) | Reaction temperature (° C.) | Reaction time (hours) | Unreacted alcohol | Intended product DM type | side product M2 type |
| Example 2 | Previously used in the preceding reaction | 0.3 | 220 | 2.3 | 1.7 | 93.3 | 3.7 |
| | | | | 2.6 | 1.0 | 93.8 | 3.8 |
| Comparative example 2 | Not used in the preceding reaction | 0.3 | 220 | 2.3 | 1.0 | 93.1 | 5.5 |

In Table 2, the "pre-reaction" refers to the reaction of a primary amine with an alcohol; the "DM type" refers to a "N-dodecyl-N,N-dimethylamine" in above examples; the "M2 type" refers to di (long-chain alkyl)- having tertiary amine, which is "N,N-didodecyl-N-methylamine" in above examples; and "% by mass to starting material" of a catalyst amount refers to "% by mass to starting alcohol" in Table 2.

The invention claimed is:

1. A method for producing a tertiary amine, comp sing reacting a secondary amine with an alcohol in the presence of a catalyst, wherein the catalyst is previously used in a reaction of a primary amine with an alcohol to obtain a tertiary amine.

2. The method according to claim 1, wherein the catalyst comprises Cu and/or Ni.

3. The method according to claim 1, wherein the primary amine is monomethylamine or monoethylamine, and the secondary amine is dimethylamine or diethylamine.

4. The method according to claim 1, wherein the primary amine is monomethylamine, and the secondary amine is dimethylamine.

5. The method according to claim 1, wherein the starting alcohol is a linear or branched, saturated or unsaturated aliphatic alcohol having 8 to 36 carbon atoms.

6. The method according to claim 1, wherein the catalyst contains Cu and Ni.

7. The method according to claim 1, wherein the catalyst contains Cu, Ni, and at least one element selected from the group consisting of Pt, Pd, Ru, and Rh.

8. The method according to claim 6, wherein a molar ratio of metal atoms Cu:Ni is 1:9 to 9:1.

9. The method according to claim 7, wherein a molar ratio of the at least one element selected from the group consisting of Pt, Pd, Ru, and Rh to the total of Cu and Ni is 0.0001 to 0.1.

10. The method according to claim 1, wherein the catalyst is used in a film form.

11. The method according to claim 1, wherein a feeding molar ratio of secondary amine/alcohol is 1 to 5.

12. The method according to claim 1, wherein a reaction temperature of the secondary amine with the alcohol is 100 to 250° C.

13. The method according to claim 1, wherein a reaction pressure of the secondary amine with the alcohol is ambient pressure to 10 atmospheres.

14. The method according to claim 1, wherein a reaction time of the secondary amine with the alcohol is 1 to 10 hours.

15. The method according to claim 1, wherein a molar ratio of the primary amine with the alcohol, primary amine/alcohol, is 0.5 to 3.

16. The method according to claim 1, wherein a reaction temperature of the primary amine with the alcohol is 100 to 250° C.

17. The method according to claim 1, wherein a reaction pressure of the primary amine with the alcohol is ambient pressure to 10 atmospheres.

18. The method according to claim 1, wherein a reaction time of the primary amine with the alcohol is 1 to 10 hours.

* * * * *